US00PP31488P3

(12) United States Plant Patent
Kleinwee

(10) Patent No.: US PP31,488 P3
(45) Date of Patent: Feb. 25, 2020

(54) ***PETUNIA* PLANT NAMED 'PEHY0033'**

(50) Latin Name: *Petunia hybrida*
Varietal Denomination: PEHY0033

(71) Applicant: SYNGENTA PARTICIPATIONS AG, Basel (CH)

(72) Inventor: Theodorus Cornelis Maria Van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,585

(22) Filed: Jul. 3, 2017

(65) Prior Publication Data

US 2018/0124980 P1 May 3, 2018

(51) Int. Cl.
*A01H 5/02* (2018.01)
*A01H 6/82* (2018.01)

(52) U.S. Cl.
USPC ..... Plt./356.1
CPC ..... *A01H 5/02* (2013.01)

(58) Field of Classification Search
USPC ..... Plt./356.1
CPC ..... A01H 5/02; A01H 6/82; A01H 5/00
See application file for complete search history.

(56) References Cited

U.S. PATENT DOCUMENTS

PP16,297 P3 * 2/2006 Iwaki ..... A01H 5/02 Plt./356.1
PP16,397 P2 * 3/2006 Kerley ..... A01H 5/02 Plt./472

OTHER PUBLICATIONS

Issuu Syngenta FloriPro Services MultiColours Brochure 2017, published on Sep. 27, 2016, retrieved on Jun. 7, 2018, retrieved from the Internet at https://issuu.com/floriproservices/docs/fps_mutlicolours_brochure_int_def, cover page, pp. 2-3,14 and 22. (Year: 2016).*
Rośliny balkonowe 2018, magra.com.pl/wp-content.../Formularz-Etykiety_2018_DYS (2).xlsx -Excel, retrieved on Jun. 5, 2018, one page. (Year: 2018).*
Syngenta Flowers North America, Sanguna Yellow (2018) retrieved on Jun. 5, 2018, retrieved from the Internet at https://www.syngentaflowers-us.com/product/flower/70061525, 2 pp. (Year: 2018).*
Canadian Food Inspection Agency for *Petunia* Pehy0005 2018, retrieved on Sep. 27, 2018, retrieved from the Internet at http://www.inspection.gc.ca/english/plaveg/pbrpov/cropreport/pet/app00008272e.shtml, one page. (Year: 2018).*
Seedstar spot. sr.o. Syngenta 2018/2019, retrieved on Jan. 24, 2019, retrieved from the Internet at https://www.seedstar.sk/assets/uploads/katalogy/e-objednavka-2018-2019.xlsx, one page. (Year: 2018).*
Syngenta Novinky balkonovek Novelties 2014/15 Annual cuttings and potplant cuttings, retrieved on Jan. 24, 2019, retrieved from the Internet at http://files.seedstar-sk.webnode.sk/200000100-063d6073a7/NOVINKY-letnicek-a-trvalek%202015.pdf, pp. 1, 9, 11-12. (Year: 2014).*
Rosliny balkonowe 2018, retrieved on Jan. 24, 2019, retrieved from the Internet at magra.com.pl/wp-content/uploads/2014/10/Formularz-Etykiety_2018_DYS.xlsx, one page. (Year: 2018).*
Syngenta Relargonia, rosliny balkonowe, rabatowe, doniczkowe, warzywa Formularz zamowienia 2016/2017, retrieved on Jul. 17, 2019, retrieved from the Internet at http://magra.com.pl/wp-content/uploads/2014/10/Formularz-rozady-i-sadzonki-2016-2017.pdf, 5 pp. (Year: 2017).*
Syngenta Google English translation, one page . (Year: 2019).*
Rosliny balkonowe 2018 retrieved from the Internet at magra.com.pl/wp-content/uploads/2014/Formularz-Etykiety_2018_DYS.xlsx, one page) (Year: 2018).*

* cited by examiner

*Primary Examiner* — June Hwu
(74) *Attorney, Agent, or Firm* — Dale Skalla

(57) ABSTRACT

A new *Petunia* plant named 'PEHY0033' particularly distinguished by medium sized, yellow flowers, mid late flowering and a semi-trailing plant habit.

1 Drawing Sheet

Latin name of the genus and species of the plant claimed: *Petunia hybrida.*

Varietal denomination: 'PEHY0033'.

BACKGROUND OF THE NEW PLANT

The present invention comprises a new *Petunia*, botanically known as *Petunia hybrida*, and hereinafter referred to by the variety name 'PEHY0033'.

'PEHY0033' is a product of a planned breeding program. The new cultivar has medium sized, yellow flowers, flowering throughout the summer, and a semi-trailing plant habit.

'PEHY0033' originated from a hybridization made in October 2011 in a controlled breeding environment in Enkhuizen, The Netherlands. The female parent was the commercial variety 'PEHY0010' Sanguna yellow (not commercial in USA), a variety that is less vigorous, has more variable color of the foliage and less intense flower color.

The male parent of 'PEHY0033' was the unpatented proprietary line 'N0322-1', a plant with lighter green foliage, less intense flower color and later flowering.

The resulting seeds were sown in January 2012. 'PEHY0033' was selected as one flowering plant within the progeny of the stated cross in May, 2012 in a controlled environment in Enkhuizen, The Netherlands.

The first act of asexual reproduction of 'PEHY0033' was accomplished when stem tip vegetative cuttings were propagated from the initial selection in June 2012 in a controlled environment in Angers, France.

BRIEF SUMMARY OF INVENTION

Horticultural examination of plants grown from cuttings of the plant initiated in June 2012 and continuing thereafter, has demonstrated that the combination of characteristics as herein disclosed for 'PEHY0033' are firmly fixed and are retained through successive generations of asexual reproduction.

'PEHY0033' has not been observed under all possible environmental conditions. The phenotype may vary significantly with variations in environment such as temperature, light intensity, and day length.

A Plant Breeder's Right for this cultivar has been applied for in the European Union on Oct. 31, 2016, No. 2016/2641. 'PEHY0033' has not been made publicly available prior to the effective filing date of this application, notwithstanding any disclosure that may have been made less than one year prior to the effective filing date of this application by the inventor or another who obtained 'PEHY0033' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0033' with colors being as true as possible with an illustration of this type.

Figure 1:
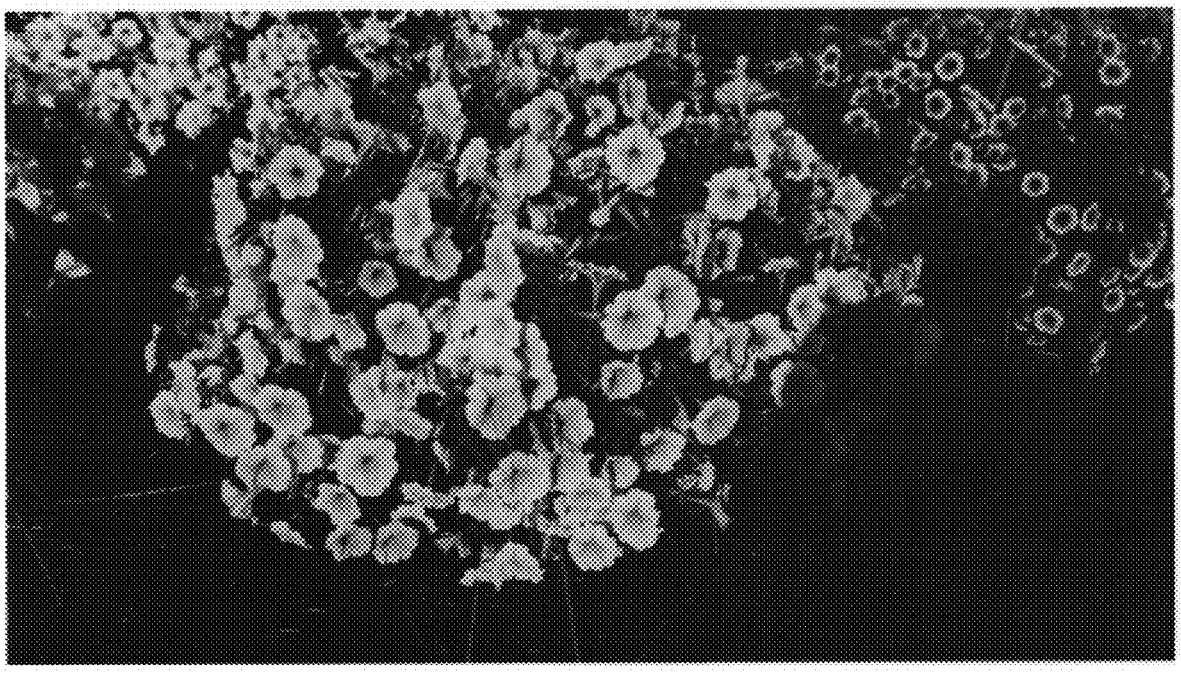
Figure 2:
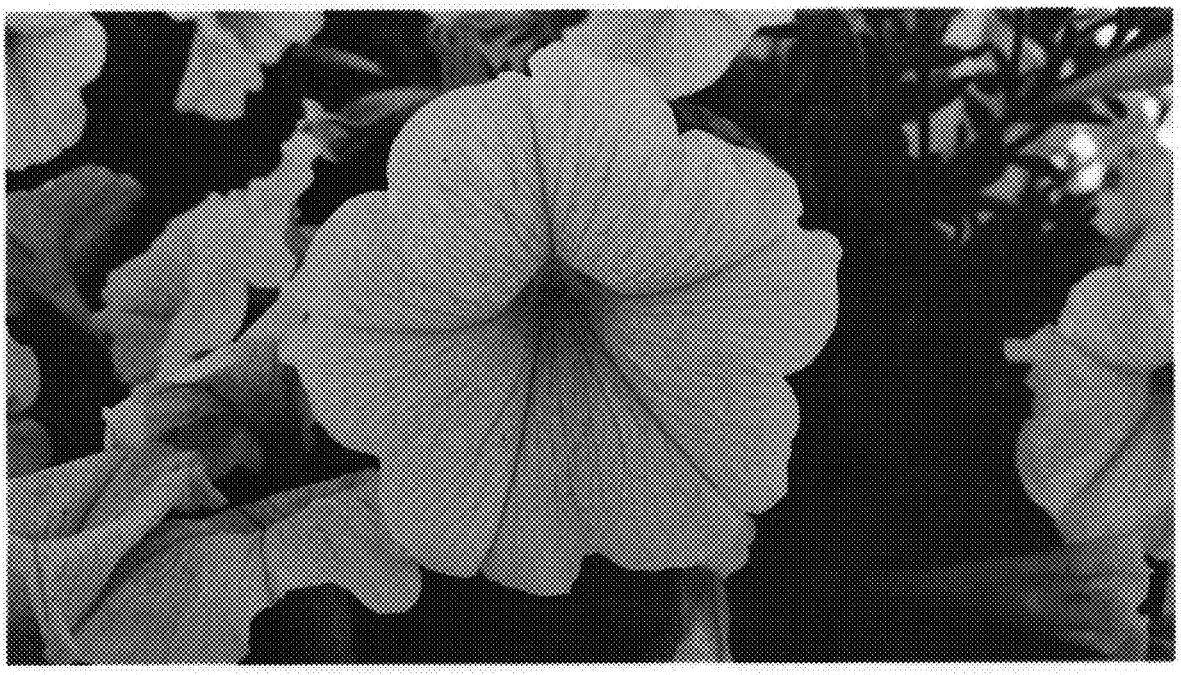

The photographic drawing shows in FIG. 1 a flowering plant of the new variety and in FIG. 2 a close-up of the flowers.

DETAILED BOTANICAL DESCRIPTION

The aforementioned photographs were taken in September 2016 from plants growing outside in Andijk, The Netherlands. These plants were approximately 22 weeks of age.

The plant descriptions and measurements were taken in October 2016 in Enkhuizen, Netherlands on 23 week old plants that were growing in 25 cm pots.

Color references are made to The Royal Horticultural Society Colour Chart (R.H.S.) 2001.

TABLE 1

DIFFERENCES BETWEEN THE NEW VARIETY 'PEHY0033' AND A SIMILAR VARIETY

| | 'PEHY0033' | 'Sunpatiki' (U.S. Plant Pat. No. 16,297) |
|---|---|---|
| Flower size: | Medium flowers (6 cm) | Small flowers (5 cm) |
| Plant Diameter: | 50 cm | 14 cm |
| Leaf Shape: | Ovate | Elliptic |

Plant:

*Form, growth and habit.*—Semi-trailing plant habit.
*Plant height.*—20 cm.
*Plant height (inflorescence included).*—22 cm.
*Plant diameter (width).*—50 cm.

Roots:

*Number of days to initiate and produce roots.*—16 days at about 22 degrees C.
*Type.*—Fine, fibrous, free branching.
*Color.*—RHS N155B.

Foliage:

*Arrangement.*—Alternate, simple.
*Immature leaf, color upper surface.*—RHS 146B.
*Immature leaf, color lower surface.*—RHS 146C.
*Mature leaf, color upper surface.*—RHS147B.
*Mature leaf, color lower surface.*—RHS 146B.
*Length.*—3 cm.
*Width.*—1.3 cm.
*Shape.*—Ovate.
*Base shape.*—Shortly Attenuate.
*Apex shape.*—Acute.
*Margin.*—Entire.
*Texture, upper surface.*—Densely covered with short hairs.
*Lower surface.*—Densely covered with short hairs.
*Color of veins, upper surface.*—RHS 146D.
*Color of veins, lower surface.*—RHS 146D.
*Petiole color.*—RHS 146D.
*Length.*—0.2 cm.
*Diameter.*—0.2 cm.
*Petiole texture.*—Densely covered with short hairs.

Stem:

*Quantity of main branches per plant.*—7-8.
*Color of stem.*—RHS 146C.
*Length of stem.*—30-35 cm.
*Diameter.*—0.4 cm.
*Length of internodes.*—1-3 cm.
*Texture.*—Dense, mostly glandular short hairs.
*Color of pedicel.*—RHS 146C.
*Length of pedicel.*—1.0-3.5 cm.
*Diameter of pedicel.*—0.2 cm.
*Texture of pedicel.*—Densely covered with short hairs.

Inflorescence:

*Type.*—Flowers solitary in upper leaf axis.
*Floret type.*—Funnel-shaped; 5 lobed petals; fused at the base.
*Blooming habit.*—Rather late flowering in greenhouse, flowering throughout the summer months.
*Quantity of inflorescences per plant.*—Approximately 50.
*Lastingness of individual blooms on the plant.*—About 7 days.
*Fragrance.*—A little scent.

Bud (just when opening):

*Color.*—RHS 154A, more yellow, RHS 1A towards top.
*Length.*—3.5 cm.
*Width.*—0.7 cm.
*Shape.*—Oblong.

Immature inflorescence:

*Flower horizontal diameter.*—4.5 cm.
*Color petals, upper surface.*—RHS 4C with darker yellow towards throat, RHS 7A green veins, RHS 149A.
*Color petals, lower surface.*—RHS 4C with green veins RHS 149A.

Mature flower:

*Flower horizontal diameter.*—6 cm.
*Flower height (vertical).*—5 cm.
*Color upper surface.*—RHS 4C with darker yellow towards throat, RHS 7A.
*Color lower surface.*—RHS 75C with green veins RHS 144B.
*All petals.*—
*Apex shape.*—Truncate to retuse.

*Margin*.—Entire.
*Waviness of margin*.—Medium.
*Petal lobation*.—Medium.
*Petal texture, upper surface*.—Papillose, glabrous.
*Petal texture, lower surface*.—Glandular hairs, more dense on veins and tube.
*Corolla tube color outside*.—RHS 1A.
*Corolla tube color inside*.—RHS 12A.
*Corolla tube length*.—3.5 cm.
*Corolla tube texture, outside*.—Spread glandular hairs of different size.
*Corolla tube texture, inside*.—Glabrous.

Calyx:
*Color of sepal, upper surface*.—RHS 147B.
*Color of sepal, lower surface*.—RHS 146B.
*Length*.—1.5 cm.
*Width*.—0.2-0.3 cm.
*Shape*.—Ensiform.
*Apex shape*.—Acute to obtuse.
*Base*.—Fused.
*Margins*.—Entire.
*Texture, upper surface*.—Densely covered with short glandular hairs.
*Lower surface*.—Densily covered with short glandular hairs.

Reproductive organs:
*Pistil*.—1.
*Length*.—2.3 cm.
*Style color*.—RHS 1D, RHS 149B near stigma.
*Style length*.—2 cm.
*Stigma color*.—RHS 145B with spots of RHS 183B.
*Stamens*.—
*Quantity per flower*.—5.
*Color of filaments*.—RHS 157D.
*Length filaments*.—2 cm.
*Anther color*.—RHS 183B.
*Anther length*.—0.15 cm.
*Anther shape*.—Elliptical.
*Color of pollen*.—RHS 158D.
*Pollen amount*.—Medium.
*Fertility/seed set*.—Has not been observed on this hybrid.
*Disease/pest resistance*.—Has not been observed on this hybrid.

What is claimed is:

1. A new and distinct variety of *Petunia* plant named 'PEHY0033' substantially as illustrated and described herein.

* * * * *